US008647323B2

(12) United States Patent
Guo et al.

(10) Patent No.: US 8,647,323 B2
(45) Date of Patent: *Feb. 11, 2014

(54) CATHETER SHAFT WITH MULTIPLE REINFORCING LAYERS AND METHOD OF ITS MANUFACTURE

(75) Inventors: Xiaoping Guo, Eden Prairie, MN (US); David Johnson, Brooklyn Park, MN (US); Richard E. Stehr, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 992 days.

This patent is subject to a terminal disclaimer.

(21) Appl. No.: 11/967,219

(22) Filed: Dec. 30, 2007

(65) Prior Publication Data

US 2009/0171319 A1 Jul. 2, 2009

(51) Int. Cl.
*A61M 25/00* (2006.01)
*B28B 5/00* (2006.01)

(52) U.S. Cl.
USPC .......................................... 604/527; 264/241

(58) Field of Classification Search
USPC .................................. 604/523–527; 264/241
See application file for complete search history.

(56) References Cited

U.S. PATENT DOCUMENTS

| | | |
|---|---|---|
| 4,776,334 A | 10/1988 | Prionas |
| 4,934,049 A | 6/1990 | Kiekhafer et al. |
| 5,248,305 A | 9/1993 | Zdrahala |
| 5,368,564 A | 11/1994 | Savage |
| 5,395,328 A | 3/1995 | Ockuly et al. |
| 5,478,330 A | 12/1995 | Imran et al. |
| 5,782,900 A | 7/1998 | de la Rama et al. |
| 5,836,946 A | 11/1998 | Diaz et al. |
| 5,851,464 A * | 12/1998 | Davila et al. ............... 264/103 |
| 5,879,499 A | 3/1999 | Corvi |
| 5,891,112 A * | 4/1999 | Samson ...................... 604/524 |
| 6,001,095 A | 12/1999 | de la Rama et al. |
| 6,235,021 B1 | 5/2001 | Sieben |
| 6,273,880 B1 | 8/2001 | Berg et al. |

(Continued)

FOREIGN PATENT DOCUMENTS

WO 2007136981 11/2007

OTHER PUBLICATIONS

International Search Report and Written Opinion for PCT/US08/85185 filed Dec. 1, 2008, dated Jan. 29, 2009.

(Continued)

*Primary Examiner* — Bhisma Mehta
*Assistant Examiner* — Bradley Osinski
(74) *Attorney, Agent, or Firm* — Wiley Rein LLP

(57) ABSTRACT

A catheter shaft includes an inner layer of a first polymeric material, an intermediate layer of a second polymeric material, an outer layer of a third polymeric material, a first wire reinforcing layer encapsulated between the inner and intermediate layers, and a second wire reinforcing layer encapsulated between the outer and intermediate layers. Typically, the first wire reinforcing layer includes one or more metallic wires helically wound in one direction and the second wire reinforcing layer includes one or more metallic wires helically wound in the opposite direction. The intermediate layer is bonded to the inner and outer layers, as by extruding layers over one another or by thermal lamination or reflow bonding. Typically, the intermediate layer has a larger yield strain and/or a lower flexural modulus and/or a lower durometer than at least one of the inner layer and the outer layer.

6 Claims, 4 Drawing Sheets

(56) References Cited

U.S. PATENT DOCUMENTS

| | | |
|---|---|---|
| 6,783,521 B2 | 8/2004 | Ponzi et al. |
| 7,229,437 B2 | 6/2007 | Johnson et al. |
| 7,234,225 B2 | 6/2007 | Johnson et al. |
| 2004/0143256 A1 | 7/2004 | Bednarek et al. |
| 2006/0095050 A1 | 5/2006 | Hartley et al. |
| 2006/0100602 A1 | 5/2006 | Klint |
| 2006/0151923 A1 | 7/2006 | Wilkowske et al. |
| 2007/0265658 A1 | 11/2007 | Nelson et al. |
| 2007/0299424 A1 | 12/2007 | Cumming et al. |
| 2008/0161762 A1 | 7/2008 | Stehr et al. |

OTHER PUBLICATIONS

International Search Report and Written Opinion for PCT/US08/84560 filed Nov. 24, 2008, dated Jan. 28, 2009.

Pebax Mechanical Properties Data Sheet, Mar. 2011, www.pebax.com.

ARKEMA, "Pebax Mechanical Properties," Pebax Polyether Block Amides 2006.

* cited by examiner

CATHETER SHAFT WITH MULTIPLE REINFORCING LAYERS AND METHOD OF ITS MANUFACTURE

CROSS-REFERENCE TO RELATED APPLICATIONS

This application is related to U.S. application Ser. No. 11/967,220, filed 30 Dec. 2007, which is hereby incorporated by reference as though fully set forth herein.

BACKGROUND OF THE INVENTION a. Field of the Invention

The instant invention relates to catheters that are used in the human body. In particular, the instant invention relates to catheters using multiple polymeric and reinforcing layers to improve kink resistance, pushability, and torqueability.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

Since the path through the patient's vasculature to the intended site is often long and tortuous, steering forces typically must be transmitted over relatively great distances. Accordingly, it is desirable for a catheter to have sufficient axial (e.g., column) strength to be pushed through the patient's vasculature via a force applied at its proximal end ("pushability"). It is also desirable for a catheter to transmit a torque applied at the proximal end to the distal end ("torqueability"). Pushability and torqueability (collectively, "maneuverability") permit a physician to manipulate a catheter to an intended site and then properly orient the catheter. It is also desirable for a catheter to have sufficient flexibility to substantially conform to the patient's vasculature and yet resist kinking as it does so. Kinking is often the result of a localized failure of the material of the catheter when localized stresses exceed the yield strength of the material.

To provide pushability, torqueability, flexibility, and kink resistance, many extant catheters are made of engineering polymer materials reinforced with metallic wire reinforcing layers. The characteristics of pushability, torqueability, flexibility, and kink resistance are often in tension with one another, however, with improvements in one requiring compromises in others.

BRIEF SUMMARY OF THE INVENTION

It is desirable to provide a catheter with improved flexibility, kink resistance, and maneuverability.

It is also desirable to provide a catheter with improved mechanical integrity.

In a first aspect, the present invention provides a method of manufacturing a catheter shaft generally including the following steps: forming an inner polymeric layer ("inner layer"); forming a first metallic-wire reinforcing layer ("first reinforcing layer") about the inner layer, the first reinforcing layer including one or more wires helically wound in a first direction at a first winding angle; forming an intermediate polymer layer ("intermediate layer") about the first reinforcing layer; forming a second metallic-wire reinforcing layer ("second reinforcing layer") about the intermediate layer, the second reinforcing layer including one or more wires helically wound in a second direction at a second winding angle; and forming an outer polymeric layer ("outer layer") about the second reinforcing layer, wherein the first direction is different from the second direction. For example, the first direction may be opposite the second direction, such as clockwise versus counter-clockwise. The first winding angle and the second winding angle are preferably between about 5 degrees and about 60 degrees, more preferably between about 10 degrees and about 20 degrees, and the first winding angle and the second winding angle may have substantially equal absolute values.

Each of the first reinforcing layer and the second reinforcing layer may include between about one and about thirty wires, more preferably between about four wires and about twenty wires. It is also within the spirit and scope of the present invention for the wires to be either single thread or multi-thread, such as a wire having more than about eight threads, and preferably having between about ten and about thirty threads. It is also contemplated that the wires may be flat wires, round wires, or a combination of both flat wires and round wires.

It is contemplated that each of the inner layer, the intermediate layer, and the outer layer will include a melt-processable polymer. Typically, a yield strain of the intermediate layer will exceed at least one of a yield strain of the inner layer and a yield strain of the outer layer, and the yield strain of the intermediate layer may exceed both the yield strain of the inner layer and the yield strain of the outer layer. It is also desirable for a durometer of the intermediate layer to be less than at least one of a durometer of the inner layer and a durometer of the outer layer. Of course, the durometer of the intermediate layer may be less than both the durometer of the inner layer and the durometer of the outer layer, for example where the inner and outer layers are made out of the same material or very similar materials (e.g., materials having approximately equal yield strains, durometers, and/or other material properties).

The inner layer, the first reinforcing layer, the intermediate layer, the second reinforcing layer, and the outer layer may be assembled layer-by-layer and then heated to form a substantially unitary catheter shaft, for example by bonding the inner layer, the intermediate layer, and the outer layer with the first and second reinforcing layers encapsulated therebetween or therein (that is, surrounded by or embedded within the catheter shaft). A heat-shrink tube may optionally be formed about the outer layer prior to heating the catheter shaft assembly.

Alternatively, the step of forming a first reinforcing layer may include helically winding one or more wires about the inner layer in the first direction; the step of forming an intermediate layer may include extruding the intermediate layer about the first reinforcing layer; the step of forming a second reinforcing layer may include helically winding one or more wires about the intermediate layer in the second direction; and the step of forming an outer layer may include extruding the outer layer about the second reinforcing layer.

In another aspect, the present invention provides a method of forming a catheter shaft generally including the following steps: forming an inner layer of a first material; forming a first wire reinforcing layer about the inner layer; forming an intermediate layer of a second material about the first wire reinforcing layer; forming a second wire reinforcing layer about the intermediate layer; and forming an outer layer of a third material about the second wire reinforcing layer, wherein the second material is hyperelastic relative to at least one of the first material and the third material.

In some embodiments, each of the first material, the second material, and the third material is selected from the group consisting of polyamides, polyurethanes, polyesters, functionalized polyolefins, polycarbonates, polyimides, polysulfones, aromatic polyketones, and any combinations thereof. In other embodiments, each of the first material, the second material, and the third material is selected from the group consisting of polyamide-based thermoplastic elastomers, polyester-based thermoplastic elastomers, thermoplastic polyurethanes, styrenic thermoplastic elastomers, ionic thermoplastic elastomers, functionalized thermoplastic polyolefins, and any combinations thereof. At least one of the first material, the second material, and the third material may optionally further include a radiopaque filler, including, but not limited to, barium sulfate, bismuth trioxide, tungsten, tantalum, gold, and the like.

Also disclosed herein is a catheter shaft formed according to a method including the steps of: forming an inner layer of a first material; forming a first wire reinforcing layer about the inner layer, the first wire reinforcing layer including one or more wires helically wound in a first direction; forming an intermediate layer of a second material about the first wire reinforcing layer; forming a second wire reinforcing layer about the intermediate layer, the second wire reinforcing layer including one or more wires helically wound in a second direction opposite the first direction; and forming an outer layer of a third material about the second wire reinforcing layer. Preferably, the second material will be hyperelastic relative to at least one of the first material and the third material, and may be hyperelastic relative to both the first material and the second material. It is also desirable for the second material to have a lower durometer than at least one of the first material and the third material.

In another embodiment, a catheter shaft according to the present invention includes: an inner layer of a first material; an intermediate layer of a second material, the intermediate layer being bonded to the inner layer; an outer layer of a third material, the outer layer being bonded to the intermediate layer; a first wire reinforcing layer encapsulated by at least one of the inner layer and the intermediate layer; and a second wire reinforcing layer encapsulated by at least one of the outer layer and the intermediate layer. Thus, for example, the first wire reinforcing layer may be entirely encapsulated by the inner layer, entirely encapsulated by the intermediate layer, or encapsulated between the inner layer and the intermediate layer. Likewise, the second wire reinforcing layer may be entirely encapsulated by the outer layer, entirely encapsulated by the intermediate layer, or encapsulated between the outer layer and the intermediate layer. Typically, the first wire reinforcing layer will include a first wire helically wound in a first direction and the second wire reinforcing layer will include a second wire helically wound in a second direction opposite the first direction.

The bond between the intermediate layer and the inner layer may result from extruding the intermediate layer over the inner layer. Similarly, the bond between the intermediate layer and the outer layer may result from extruding the outer layer over the intermediate layer. Alternatively, the bond between the intermediate layer and the inner layer may result from heat-laminating (or reflow bonding) the intermediate layer to the inner layer, and the bond between the outer layer and the intermediate layer may result from heat-laminating (or reflow bonding) the outer layer to the intermediate layer. Accordingly, it is desirable for the second material to be chemically bondable with both the first material and the second material.

An advantage of the present invention is that it provides a catheter having increased flexibility and kink resistance.

Another advantage of the present invention is that it enhances mechanical integrity of the catheter having increased torqueability and axial (or column) strength.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a catheter shaft suitable for use in the human vasculature for known medical procedures, such as cardiac mapping and ablation. Catheters utilizing catheter shafts according to the present invention advantageously exhibit improved maneuverability, flexibility, and kink resistance. For purposes of this description, the invention will be described in connection with an elongate electrophysiology catheter. It is contemplated, however, that the described features and methods may be incorporated into any number of catheters (e.g., steerable catheters, introducer catheters, and the like) as would be appreciated by one of ordinary skill in the art.

Figure 1:
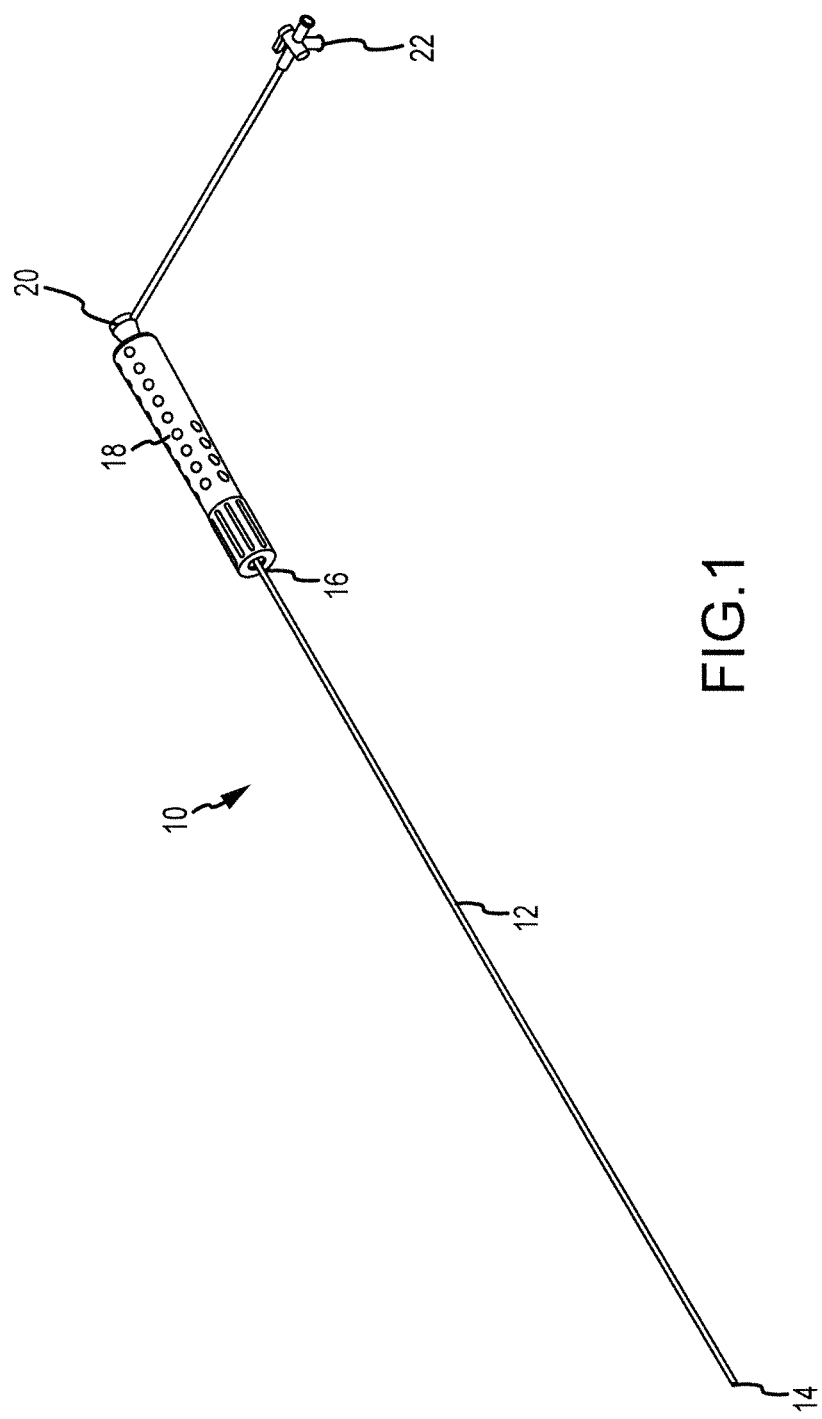
FIG. 1 is a perspective view of an exemplary catheter according to an embodiment of the present invention.

Referring now to the figures, and in particular to FIG. 1, an electrophysiology catheter 10 includes a shaft 12 having a distal end 14 and a proximal end 16. A handle 18 may be coupled to proximal end 16 of shaft 12 to control catheter 10 (e.g., to push and/or torque catheter 10). Catheter 10 may also include a hub 20 operably coupled to an inner lumen (not shown) within handle 18. A valve 22 may be operably connected to hub 20. Of course, it is also contemplated that any known device for manipulation of catheter 10 may be coupled to proximal end 16 thereof, including, without limitation, robotic manipulation devices and the like.

The basic method of manufacture of catheter 10, and in particular of at least a portion of shaft 12, according to an embodiment of the present invention will be described with reference to FIGS. 2-6. As they are assembled, the catheter components will be collectively referred to as a "catheter shaft assembly."

Figure 2:
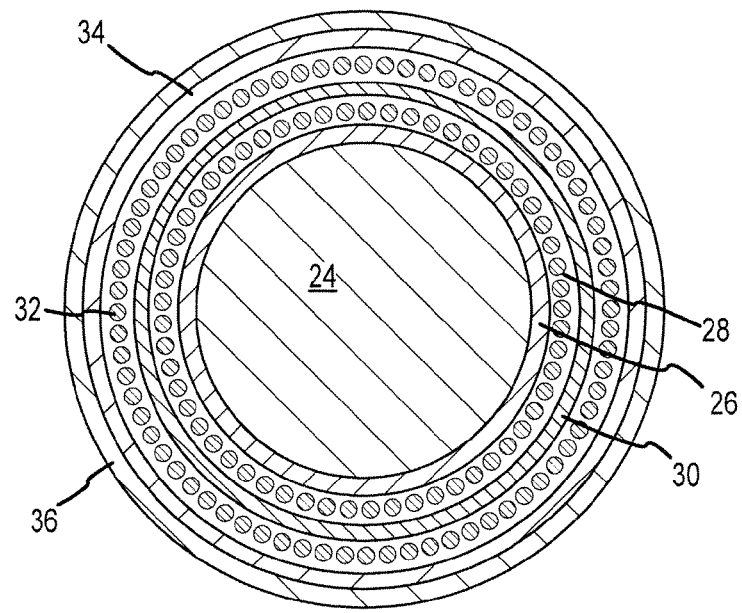
FIG. 2 is an axial cross-sectional view of the various components of a catheter shaft assembly according to an embodiment of the present invention prior to the application of energy to melt process the catheter shaft assembly.

As depicted in FIG. 2, a mandrel or hypotube 24, which is preferably round in cross-section and preferably from about 6 inches to about 4 feet in length, is a component of the catheter shaft assembly, and may be the first component thereof during manufacture of catheter shaft 12. Typically, mandrel 24 is disposable. Mandrel 24 has a distal end and a proximal end. An inner layer 26 is formed or introduced about mandrel 24. For example, inner layer 26 may be knotted at one end (e.g., the distal end) and then fed onto mandrel 24.

Inner layer 26 may be an extruded polymeric tubing, such as extruded polytetrafluoroethylene (PTFE) tubing (e.g., Teflon® brand tubing), optionally including surface etching. One of ordinary skill will also appreciate that inner layer 26 may be made of other fluoropolymers, including, without limitation, fluorinated ethylene-propylene copolymer (FEP), perfluoroalkoxyethylene (PFA), poly(vinylidene fluoride), poly(ethylene-co-tetrafluoroethylene), and other fluoropolymers with surface treatments for bonding, as well as any combinations thereof. Inner layer 26 may also be made of melt-processable thermoplastic elastomeric polymers, including, without limitation, polyether block amides, styrenic thermoplastic elastomers, polyester-based thermoplastic elastomers, thermoplastic polyurethanes, ionic thermoplastic elastomers, functionalized thermoplastic polyolefins, and any combinations thereof. One such elastomer is Pebax®, made by Arkema, Inc. Pebax of various durometers may be used, including, without limitation, Pebax 30D to Pebax 72D. In general, suitable materials for inner layer 26 include, without limitation, polyamides, polyurethanes, polyesters, functionalized polyolefins, polycarbonates, polysulfones, and any combinations thereof. Specific suitable materials for inner layer 26 include, without limitation, Pebax® 7233, Fina TR140, Amoco 9433X, Grilamid L25, and Rilsan BESNO TL, and Makrolon 3108.

Figure 3:
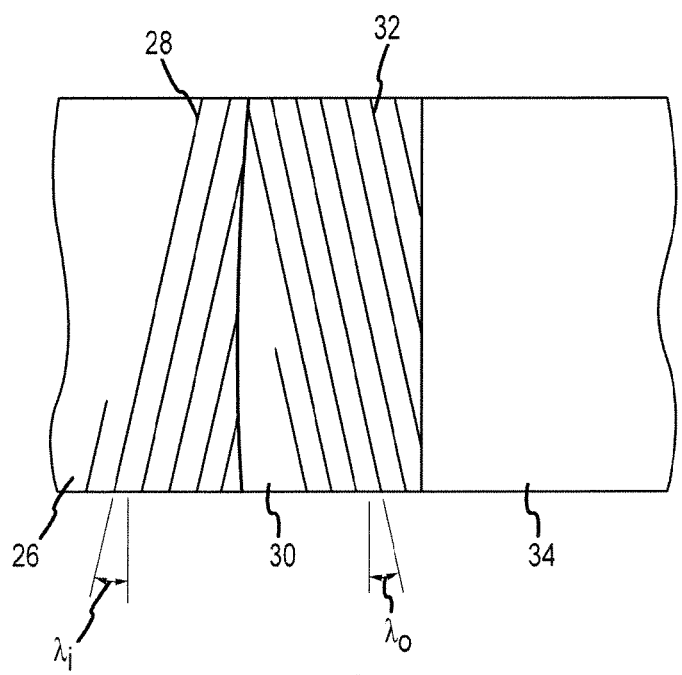
FIG. 3 is a cut-away view of a catheter shaft according to an embodiment of the present invention illustrating various layers thereof.

A first reinforcing layer 28 may then be formed about inner layer 26. First reinforcing layer 28 may be formed of stainless steel wire, including, for example, 306V stainless steel wire. Of course, high strength synthetic fibers made of high performance engineering polymer materials may be used in first reinforcing layer 28 (e.g., Kevlar® fibers and the like). As shown in FIG. 3, first reinforcing layer 28 is preferably one or more wires helically wound in a first direction (e.g., clockwise or counter-clockwise) at a first angle $\lambda_i$. $\lambda_i$ is preferably between about five degrees and about sixty degrees, and more preferably between about fifteen degrees and about twenty degrees. First reinforcing layer 28 preferably includes between about one wire and about thirty wires, and more preferably between about four wires to about twenty wires. Alternatively, first reinforcing layer 28 may be characterized by varying winding angle (thus, the term "winding angle" as used herein refers to both substantially constant and varying winding angles) and/or number of wires.

First reinforcing layer 28 may be formed separately on a disposable core and slipped about inner layer 26. Alternatively, first reinforcing layer 28 may be wound directly upon inner layer 26. In addition, one or more portions of first reinforcing layer 28 may be heat tempered and cooled before incorporation into the catheter shaft assembly through methods that are known to those of ordinary skill in the art. The action of heat tempering may help to release the stress on the wire and help reduce radial forces.

Returning now to FIG. 2, an intermediate layer 30, typically of a melt-processing polymer, is formed about first reinforcing layer 28. In some embodiments of the invention, intermediate layer 30 is extruded about first reinforcing layer 28. In other embodiments of the invention, intermediate layer 30 is separately extruded and then slipped about first reinforcing layer 28 as part of the catheter shaft assembly. Intermediate layer 30 will be discussed in further detail below.

Next, a second reinforcing layer 32 may be formed about intermediate layer 30. Second reinforcing layer 32 may be formed of stainless steel wire, including, for example, 306V stainless steel wire. Of course, high strength synthetic fibers made of high performance engineering polymer material may be used in second reinforcing layer 32 (e.g., Kevlar® fibers and the like). As shown in FIG. 3, second reinforcing layer 32 is preferably one or more wires helically wound in a second direction (e.g., clockwise or counter-clockwise) at a second angle $\lambda_o$. $\lambda_o$ is preferably between about five degrees and about sixty degrees, more preferably between about fifteen degrees and about twenty degrees. Second reinforcing layer 32 preferably includes between about one wire and about thirty wires, and more preferably between about four wires to about twenty wires. Alternatively, second reinforcing layer 32 may be characterized by varying winding angle (thus, the term "winding angle" as used herein refers to both substantially constant and varying winding angles) and/or number of wires.

As illustrated in FIG. 3, second reinforcing layer 32 is wound in a direction opposite first reinforcing layer 28. First and second reinforcing layers 28, 32 may be wound at substantially equal winding angles and/or winding pitches or at differing winding angles and/or winding pitches. One of ordinary skill in the art will appreciate how to select winding angles and/or the number of wires for first and second reinforcing layers 28, 32 for a particular application of catheter 10.

Second reinforcing layer 32 may be formed separately on a disposable core and slipped about intermediate layer 30. Alternatively, second reinforcing layer 32 may be wound directly upon intermediate layer 30. In addition, one or more portions of second reinforcing layer 32 may be heat tempered and cooled before incorporation into the catheter shaft assembly through methods that are known to those of ordinary skill in the art. The action of heat tempering may help to release the stress on the wire and help reduce radial forces.

It is contemplated that either single thread or multi-thread wire may be used to form first reinforcing layer 28 and second reinforcing layer 32. Thus, both first reinforcing layer 28 and second reinforcing layer 32 may use single thread wire, both may use multi-thread wire, or one may use single thread wire and the other multi-thread wire. Where multi-thread wire is used, it is preferred that the wire include about eight or more threads, and more preferably between about ten threads and about thirty threads.

It is also contemplated that the wires forming first and second reinforcing layers 28, 32 may be flat wires (that is, generally ribbon-like wires), round wires (that is, wires having a generally circular axial cross-section), or a combination of flat wires and round wires.

For purposes of this invention, a "flat wire" refers to a wire that is characterized by an axial cross section that, when measured along two orthogonal axes, is substantially flat. A flat wire typically has a rectangular axial cross-section. For example, the axial cross-sectional dimensions of the first wire may be approximately 0.001" by about 0.005". Of course, the axial cross-section need not be perfectly rectangular. For example, the present invention contemplates that the axial cross-section of the flat wire may be oval, provided that the overall axial cross-section is generally flat. For example, a wire may be properly characterized as a flat wire if it has an axial cross-section that is measured X in one direction and at least 3× in a second direction generally orthogonal to the first direction. A wire whose axial cross-section is substantially I-shaped may also be a flat wire if, generally, its height is substantially greater than its width at its widest measurement.

One of ordinary skill will appreciate that a flat wire may be defined in the context of the overall teachings of this application.

Referring again to FIG. 2, an outer layer 34 may be formed about second reinforcing layer 32. In some embodiments of the invention, outer layer 34 is extruded about second reinforcing layer 32. In other embodiments of the invention, outer layer 34 is separately extruded and then slipped about second reinforcing layer 32 as part of the catheter shaft assembly.

Outer layer 34 is typically a melt-processable polymeric tube, such as an extruded polytetrafluoroethylene (PTFE) tubing (e.g., Teflon® brand tubing), optionally including surface etching. Outer layer 34 may also be made of other melt processing polymers, including, without limitation, etched polytetrafluoroethylene and other fluoropolymers, poly(ether block amide)s, thermoplastic polyurethanes, polyester-based thermoplastic elastomers, and other thermoplastic elastomers. One such elastomer is Pebax®, made by Arkema, Inc. Pebax of various durometers may be used, including, without limitation, Pebax 30D to Pebax 72D. Of course, one of ordinary skill in the art will recognize that various thermoplastics described as suitable for use as inner layer 26 (e.g., polyamides, polyesters, polycarbonate, polyurethane, polyolefins, polysulfones, polyimides, liquid crystal polymers, aromatic polyketones, and the like) are also generally suitable for use as outer layer 34. One of ordinary skill will also appreciate that the material of outer layer 34 may be different from or the same as the material of inner layer 26 as desired, and will further appreciate how to select suitable materials for inner layer 26 and outer layer 34 for a particular application of catheter 10.

Preferably, intermediate layer 30 will be of a different material than inner layer 26 and outer layer 34. In particular, in some embodiments of the invention, intermediate layer 30 will be hyperelastic relative to at least one of, and preferably both of, inner layer 26 and outer layer 34. That is, intermediate layer 30 may have a lower flexural modulus and a higher yield strain than either or both of inner layer 26 and outer layer 34. The lower flexural modulus and higher yield strain of intermediate layer 30 relative to inner layer 26 and/or outer layer 34 advantageously promotes maneuverability of catheter shaft 12. It is also desirable for intermediate layer 30 to have a lower durometer than at least one of, and preferably both of, inner layer 26 and outer layer 34. Preferably, intermediate layer 30 is made of a hyperelastic polymer material having a durometer between about 25 D and about 70 D, more preferably between about 40 D and about 60 D, and a yield strain greater than about 5%, more preferably greater than about 8%.

Suitable materials for intermediate layer 30 include, without limitation, polyamides, polyesters, polyurethanes, functionalized polyolefins, polyamide-based thermoplastic elastomers, polyester-based thermoplastic elastomers, styrenic thermoplastic elastomers, functionalized thermoplastic olefins, thermoplastic polyurethanes, ionic thermoplastic elastomers, and any combinations thereof. Specifically suitable materials for intermediate layer 30 include, without limitation, Pebax® 6033, Pellethane 2163-60, Pellethane 2163 65D, Fusabond®N MN493D, Fusabond®E MB100D, Fusabond®P M613-05, and Pebax® 6833.

The thickness of inner layer 26 and outer layer 34 may be the same or different. The thickness of intermediate layer 30 may be equal to or less than the thickness of either or both of inner layer 26 and outer layer 34. Typically, intermediate layer 30 will be thinner than both inner layer 26 and outer layer 34.

It is desirable for there to be at least partial chemical compatibility between intermediate layer 30 and inner layer 26 and between intermediate layer 30 and outer layer 34. This will promote bonding between the layers of the catheter shaft assembly and reduce the likelihood of strain-induced polymer delamination under manipulation of catheter 10. Such compatibility may be provided by forming inner layer 26 and outer layer 34 of material pairs whose polarity and/or solubility parameter are similar to that of intermediate layer 30. Alternatively, or additionally, chemical modifications may be undertaken to achieve at least partial chemical compatibility between these polymeric layers. For example, intermediate layer 30 may be blended and/or compounded with a minor amount of the material of inner layer 26 and/or outer layer 34. In other embodiments, one or more of inner layer 26, intermediate layer 30, and outer layer 34 may include a coupling agent, such as silanes, zirconates, titanates, and the like. In still other embodiments of the invention, one or more of inner layer 26, intermediate layer 30, and outer layer 34 may include polymeric modifiers or adhesion promoters.

One of ordinary skill in the art will recognize how to select or fashion compatible materials for inner layer 26, intermediate layer 30, and outer layer 34, though certain exemplary embodiments of the invention are provided below. In addition, selection of material layers is also described in U.S. application Ser. No. 11/967,220, filed 30 Dec. 2007.

In some embodiments of the invention, it is desirable for the catheter shaft assembly to be radiopaque. Thus, it is contemplated that one or more of inner layer 26 and outer layer 34 may include a radiopaque filler. Suitable radiopaque fillers include, without limitation, barium sulfate, bismuth subcarbonate, bismuth trioxides, bismuth oxychloride, tungsten, tantalum, platinum, gold, and any combinations thereof. Radiopaque nanoclays may also be employed. Typically, intermediate layer 30 will not include such radiopaque fillers, but doing so is not outside of the spirit and scope of the present invention. As an alternative to the use of radiopaque fillers, or in addition to the use of radiopaque fillers, a radiopaque marker (not shown) may be included in the catheter shaft assembly.

Figure 4:
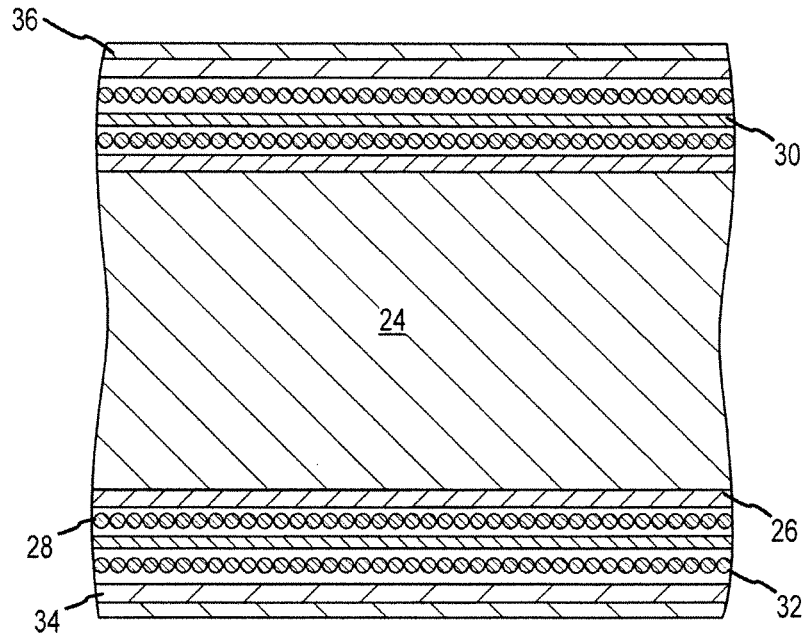
FIG. 4 is a longitudinal cross-sectional view of the various components of a catheter shaft assembly according to an embodiment of the present invention prior to the application of energy to melt process the catheter shaft assembly.

FIG. 2 displays an axial-cross section of the catheter shaft assembly including inner layer 26, first reinforcing layer 28, intermediate layer 30, second reinforcing layer 32, and outer layer 34 before forming a catheter shaft, which may be accomplished by lamination of the various layers by heating (e.g., reflow bonding). FIG. 4 depicts a longitudinal cross-section of the catheter shaft assembly at the same stage of manufacture. In some embodiments of the invention, a layer of heat shrink 36 is placed over outer layer 34 as depicted in FIGS. 2 and 4. Heat shrink 36 is preferably a fluoropolymer or polyolefin material such as polytetrafluoroethylene (PTFE) or fluorinated ethylene-propylene copolymer (FEP). As an alternative to heat shrink tube 36, the catheter shaft assembly may be placed into a suitable mold prior to subsequent processing. Either heat shrink tube 36 or a suitable mold may be generally referred to as a "shape retention structure," so named because it retains the overall shape of the catheter shaft assembly (that is, the generally circular axial cross-section) during melt-processing.

Figure 5:
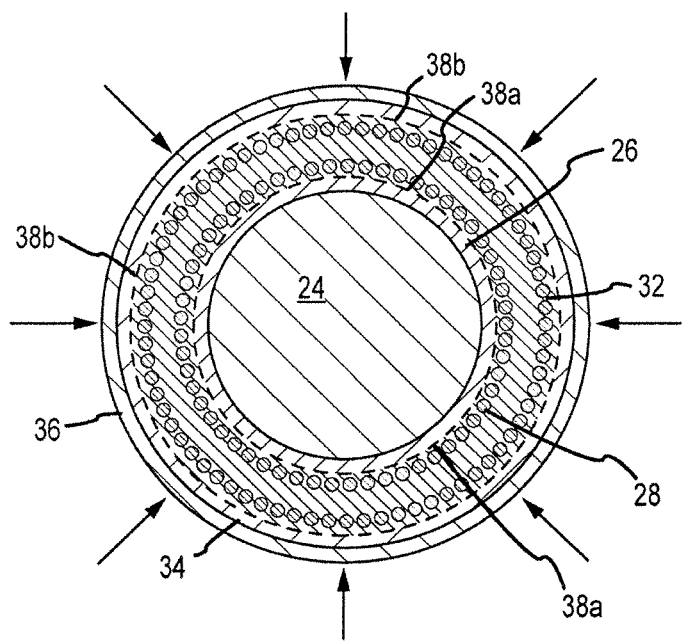
FIG. 5 is an axial cross-sectional view of a catheter shaft assembly according to an embodiment of the present invention during the application of energy to melt process the catheter shaft assembly.

As shown in FIG. 5, the catheter shaft assembly may then be melt-processed. Energy (e.g., radiofrequency energy or thermal energy) is applied to the catheter shaft assembly, for example to the outer surface of the catheter shaft assembly, to bond inner layer 26, intermediate layer 30, and outer layer 34 together in a process often referred to as "reflow bonding." Heat shrink tube 36 has a higher melting or softening temperature than inner layer 26, intermediate layer 30, and outer layer 34, such that, during the melting process, heat shrink tube 36 will contract while retaining its tubular shape. The combination of applied energy and pressure exerted by heat shrink tube 36 forces melted inner layer 26, intermediate layer 30, and outer layer 34 to flow and redistribute about the circumference of the catheter shaft assembly and bond together, as represented by interphase lines 38a (between inner layer 26 and intermediate layer 30) and 38b (between outer layer 34 and intermediate layer 30).

Once the catheter shaft assembly has cooled, mandrel 24 can be removed, leaving a central lumen 40 (FIG. 6) extending through at least a portion of formed catheter shaft 12. Optionally, heat shrink tube 36 may also be removed, such that outer layer 34 becomes the outermost layer of the catheter shaft assembly.

Figure 6:
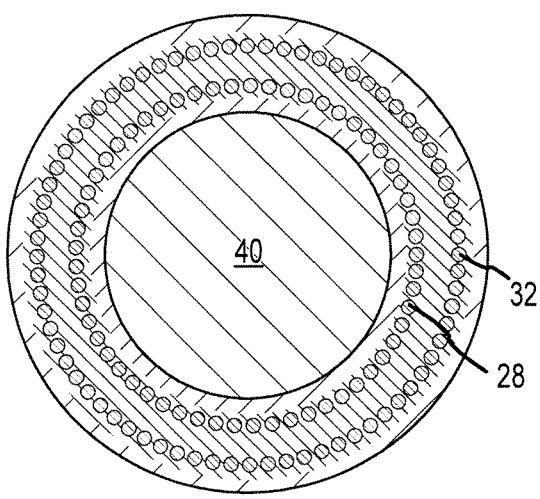
FIG. 6 is an axial cross-sectional view of a catheter shaft according to an embodiment of the present invention after the application of energy to melt process the catheter shaft assembly into the catheter shaft.

FIG. 6 depicts the catheter shaft assembly after the conclusion of the reflow bonding process (that is, FIG. 6 depicts an axial-cross section of a catheter shaft formed according to an embodiment of the present invention). One of skill in the art will appreciate that, as a result of the reflow bonding process described above, first reinforcing layer 28 will be encapsulated by inner layer 26 and/or intermediate layer 30, while second reinforcing layer 32 will be encapsulated by outer layer 34 and/or intermediate layer 30. Thus, it is within the spirit and scope of the invention for first and second reinforcing layers 28, 32 to be entirely encapsulated within intermediate layer 30 near the respective interfaces with inner and outer layers 26, 34, to be entirely encapsulated within inner and outer layers 26, 34, respectively, or to be partially encapsulated by each layer along the interface between layers. Advantageously, the interfaces (e.g., bonds) between inner layer 26 and intermediate layer 30 and between outer layer 34 and intermediate layer 30 are substantially seamless without any dead spaces or material voids covered by the wires used in the first and second reinforcing layers 28, 32. This reduces the likelihood of material cracking and other failures of catheter shaft 12.

As described above, intermediate layer 30 may be hyperelastic relative to at least one, and preferably both of, inner layer 26 and outer layer 34. In addition, first and second reinforcing layers 28, 32 are wound in opposite directions. These features advantageously permit a catheter shaft according to the present invention to effectively undertake bidirectional torques and axial forces with improved kink resistance and mechanical integrity, even when the catheter shaft is under flexural loading.

The following tables provide several exemplary embodiments of a catheter shaft formed according to the present invention.

TABLE 1

| | |
|---|---|
| Inner Layer | Pebax 7233 filled with 30% BaSO$_4$ fillers |
| 1$^{st}$ Reinf. Layer | 306 V stainless steel wire, 0.001" by 0.005", 8 threads, counter-clockwise |
| Intermediate Layer | Pebax 6033 |
| 2$^{nd}$ Reinf. Layer | 306 V stainless steel wire, 0.001" by 0.005", 8 threads, clockwise |
| Outer Layer | Pebax 7233 filled with 30% BaSO$_4$ fillers |

TABLE 2

| | |
|---|---|
| Inner Layer | Pebax 7233 filled with 30% BaSO$_4$ fillers |
| 1$^{st}$ Reinf. Layer | 306 V stainless steel wire, 0.001" by 0.005", 8 threads, counter-clockwise |
| Intermediate Layer | Pellethane 2163-60 |
| 2$^{nd}$ Reinf. Layer | 306 V stainless steel wire, 0.001" by 0.005", 8 threads, clockwise |
| Outer Layer | Pebax 7233 filled with 30% BaSO$_4$ fillers |

TABLE 3

| | |
|---|---|
| Inner Layer | Pebax 7233 filled with 30% BaSO$_4$ fillers |
| 1$^{st}$ Reinf. Layer | 306 V stainless steel wire, 0.001" by 0.005", 8 threads, counter-clockwise |
| Intermediate Layer | Pellethane 2163-65D |
| 2$^{nd}$ Reinf. Layer | 306 V stainless steel wire, 0.001" by 0.005", 8 threads, clockwise |
| Outer Layer | Pebax 7233 filled with 30% BaSO$_4$ fillers |

TABLE 4

| | |
|---|---|
| Inner Layer | Pebax 7233 filled with 30% BaSO$_4$ fillers |
| 1$^{st}$ Reinf. Layer | 306 V stainless steel wire, 0.001" by 0.005", 8 threads, counter-clockwise |
| Intermediate Layer | Pellethane 2163-65D |
| 2$^{nd}$ Reinf. Layer | 306 V stainless steel wire, 0.001" by 0.005", 8 threads, clockwise |
| Outer Layer | Makrolon 3108 filled with 30% BaSO$_4$ fillers |

TABLE 5

| | |
|---|---|
| Inner Layer | Fina TR140 filled with 30% BaSO$_4$ fillers |
| 1$^{st}$ Reinf. Layer | 306 V stainless steel wire, 0.001" by 0.005", 8 threads, counter-clockwise |
| Intermediate Layer | Fusabond-N MN493D |
| 2$^{nd}$ Reinf. Layer | 306 V stainless steel wire, 0.001" by 0.005", 8 threads, clockwise |
| Outer Layer | Pebax 7233 filled with 30% BaSO$_4$ fillers |

TABLE 6

| | |
|---|---|
| Inner Layer | Fina TR140 filled with 30% BaSO$_4$ fillers |
| 1$^{st}$ Reinf. Layer | 306 V stainless steel wire, 0.001" by 0.005", 8 threads, counter-clockwise |
| Intermediate Layer | Fusabond ® E MB100D |
| 2$^{nd}$ Reinf. Layer | 306 V stainless steel wire, 0.001" by 0.005", 8 threads, clockwise |
| Outer Layer | Pebax 7233 filled with 30% BaSO$_4$ fillers |

TABLE 7

| | |
|---|---|
| Inner Layer | Amoco 9433X filled with 30% BaSO$_4$ fillers |
| 1$^{st}$ Reinf. Layer | 306 V stainless steel wire, 0.001" by 0.005", 8 threads, clockwise, helical angle of 20° |
| Intermediate Layer | Fusabond ® M613-05 |
| 2$^{nd}$ Reinf. Layer | 306 V stainless steel wire, 0.001" by 0.005", 16 threads, counter-clockwise, helical angle of 15° |
| Outer Layer | Pebax 7233 filled with 30% BaSO$_4$ fillers |

TABLE 8

| | |
|---|---|
| Inner Layer | Rilsan BESNO TL filled with 30% BaSO$_4$ fillers |
| 1$^{st}$ Reinf. Layer | 306 V stainless steel wire, 0.001" by 0.005", 8 threads, clockwise, helical angle of 20° |
| Intermediate Layer | Pebax 6833 |
| 2$^{nd}$ Reinf. Layer | 306 V stainless steel wire, 0.001" by 0.005", 16 threads, counter-clockwise, helical angle of 15° |
| Outer Layer | Makrolon 3108 filled with 30% BaSO$_4$ fillers |

Although several embodiments of this invention have been described above with a certain degree of particularity, those skilled in the art could make numerous alterations to the disclosed embodiments without departing from the spirit or scope of this invention. For example, a catheter formed according to the present invention may have varying sizes and varying uses, including, but not limited to, the treatment of atrial fibrillation and the treatment of atrial tachycardia. In addition, it is contemplated that either or both of first reinforcing layer 28 and second reinforcing layer 32 may include multiple wires rather than single wires.

One of ordinary skill in the art will also appreciate that other modifications could be made to the catheter shaft assembly herein without departing from the spirit and scope of the present invention. For example, the catheter shaft assembly could be made steerable, for example as described in U.S. application Ser. No. 11/647,313, filed 29 Dec. 2006 ("the '313 application"), or with embedded internal components, for example as described in U.S. application Ser. No. 11/646,578, filed 28 Dec. 2006 ("the '578 application"). Both the '313 application and the '578 application are hereby incorporated by reference as though fully set forth herein.

In addition, it is contemplated that a catheter according to the present invention may be manufactured using alternative techniques. For example, rather than bonding the layers of the catheter shaft assembly via melt lamination processing (e.g., reflow bonding) as generally described above, one or more layers may be extruded over one another (e.g., extrusion of intermediate layer 30 over first reinforcing layer 28). Of course, it is also within the spirit and scope of the invention to utilize a combination of reflow bonding and extrusion processes (e.g., reflow bonding intermediate layer 30, first reinforcing layer 28, and inner layer 26, followed by winding of second reinforcing layer 32 and extrusion of outer layer 34 thereabout). As another example, the various polymeric layers may be formed by wrapping or winding a suitable material about the catheter shaft assembly (e.g., wrapping a chemically-etched PTFE tape about mandrel 24 to form inner layer 26).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter shaft formed according to a method comprising the steps of:
    forming an inner layer of a first material;
    forming a first wire reinforcing layer about the inner layer, the first wire reinforcing layer comprising one or more wires helically wound in a first direction;
    forming an intermediate layer of a second material about the first wire reinforcing layer;
    forming a second wire reinforcing layer about the intermediate layer, the second wire reinforcing layer comprising one or more wires helically wound in a second direction opposite the first direction; and
    forming an outer layer of a third material about the second wire reinforcing layer,
    wherein the second material has a lower flexural modulus and a higher yield strain than at least one of the first material and the third material.

2. The catheter shaft according to claim 1, wherein the second material has a lower durometer than at least one of the first material and the third material.

3. A catheter shaft, comprising:
    an inner layer of a first material;
    an intermediate layer of a second material, the intermediate layer being bonded to the inner layer;
    an outer layer of a third material, the outer layer being bonded to the intermediate layer;
    a first wire reinforcing layer encapsulated by at least one of the inner layer and the intermediate layer; and
    a second wire reinforcing layer encapsulated by at least one of the outer layer and the intermediate layer,
    wherein the first wire reinforcing layer comprises a first wire helically wound in a first direction and the second wire reinforcing layer comprises a second wire helically wound in a second direction opposite the first direction,
    wherein the intermediate layer is hyperelastic relative to at least one of the inner layer and the outer layer.

4. The catheter shaft according to claim 3, wherein the intermediate layer is hyperelastic relative to both the inner layer and the outer layer.

5. The catheter shaft according to claim 3, wherein the second material is chemically bondable with both the first material and the second material.

6. The catheter shaft according to claim 3, wherein at least one of the first material, the second material, and the third material is radiopaque.

* * * * *